United States Patent [19]

Hall et al.

[11] Patent Number: 5,182,306
[45] Date of Patent: Jan. 26, 1993

[54] USE OF COLCHICINE FOR THE CONTROL OF RETROVIRUSES

[75] Inventors: William W. Hall, New York, N.Y.; Stanley E. Read, Toronto, Canada; Michael Lyons, Irvington; John B. Zabriskie, New York, both of N.Y.

[73] Assignee: The Rockefeller University, New York, N.Y.

[21] Appl. No.: 746,283

[22] Filed: Aug. 12, 1991

Related U.S. Application Data

[63] Continuation of Ser. No. 412,638, Sep. 25, 1989, abandoned, which is a continuation of Ser. No. 208,752, Jun. 17, 1988, abandoned.

[51] Int. Cl.$^5$ ............................................. H61K 31/16
[52] U.S. Cl. ..................................................... 514/629
[58] Field of Search ......................... 514/629; 412/638

[56] References Cited

U.S. PATENT DOCUMENTS 4,190,673  2/1980  Eakins et al. ....................... 514/629

OTHER PUBLICATIONS

Physicians' Desk Reference 38 ed, 1984, pp. 1119–1120.
Satake et al., J. Gen. Virol 58:339 et seq. (1982) (Applicants should provide a copy of this reference note p. 6–lines 2 and 3 of specification).

*Primary Examiner*—Jerome D. Goldberg
*Attorney, Agent, or Firm*—Wyatt, Gerber, Burke & Badie

[57] ABSTRACT

This invention relates to treating vetrovirus of the leutivirous group with colchicine.

2 Claims, No Drawings

USE OF COLCHICINE FOR THE CONTROL OF RETROVIRUSES

This application is a continuation of application Ser. No. 07/412,638, filed Sep. 25, 1989, now abandoned, which is a continuation of Ser. No. 07/208,752, filed Jun. 16, 1988, now abandoned.

This invention is concerned with methods of treating humans infected with retroviruses of the lentivirus subgroup. Retroviruses are a well known class of viruses characterized by the presence of an RNA genome which is copied (transcribed) into DNA in the infected cell by an enzyme, reverse transcriptase (RT) which comes prepackaged in the infecting virus. Lentivirus is a subgroup of retrovirus characterized by the fact that the manifestation of infection in humans may take many years. The virus, after the initial invasion, may lie dormant for a long period of time, even several years, notably in the macrophages and then suddenly become activated when the right set of environmental circumstances is present.

Several species of such lentivirus are known and recognized. These include, for example the human immunodeficiency viruses HIV-1 and HIV-2 responsible for the disease known as the Acquired Immune Deficiency Syndrome (AIDS) and HTLV the human T-cell lymphotropic virus which causes T-cell lymphomas, certain leukemias and tropical spastic paraparesis. This invention is applicable to these and other retroviruses having like activity.

The viral replication cycle, i.e., the multiplication of the virus, or spread of the infection in the human system is through attachment to cell receptor of the T-cell (the $T_4$ cell and macrophage in the case of an HIV virus), penetration of the cell outer membrane, uncoating of the retrovirus, transcription of viral RNA to DNA through the action of RT, integration of viral DNA into host chromosomes, and several other steps terminating with the generation of new virus particles containing RNA by known and understood mechanisms.

It should be possible to control and prevent replication by interference at any one of the several steps.

The presently preferred procedure for treating AIDS is by treatment with AZT (3'-azido-3'-deoxy thymidine). It is a nucleoside analog which is a competitive inhibitor as a nucleoside triphoshate of the RT of HIV or other retroviruses. It adds on to the growing DNA chain by the typical 3',5' phosphodiester link, but since its own 3' position is blocked by an azido group, no further addition to the DNA chain is possible. Thus chain termination and failure of replication results.

At the high doses required for oral administration in the treatment of humans there are significant hematological toxicities, with severe leucopenia resulting in up to 20% of the patients. Other side effects include rash puritis, nausea, headache, and occasional CNS toxicity with focal status epilepticus Another drug utilized for treatment of AIDS is Suramin. This drug is a well known anti-trypanosomal agent. It was the prototype agent shown to be effective against HIV in vitro. It is a potent inhibitor of the RT of retroviruses in vitro where it seemingly interacts with the template-primer binding site of the enzyme. Side effects in humans include fever, rash, pyuria, proteinurea, neutropenia, paresthesia, and adrenal insufficiency.

The strategy involved in the use of such drugs as AZT and Suramin is to inhibit HIV replication in the cells at the stage of reverse transcription of the viral genome RNA into DNA, i.e., DNA synthesis on an RNA template. However these compounds also interfere with normal DNA-dependent DNA synthesis as well. This results in severe side effects on tissue such as bone marrow, especially over periods of prolonged use.

Clearly there is a need for improved methods for treating HIV and other retrovirus infections.

Colchicine is N-(5,6,7,9-tetrahydro-1,2,3,10 tetramethoxy-9-oxabenzo [a] heptalen-7-yl) acetamide, $C_{22}H_{25}NO_6$. It is an alkaloid tropolone derivative isolated from the seeds of colchicum autumnale. It has long been known as a therapeutic agent for humans, particularly as a gout suppressant and in the treatment of familial Mediterranean fever. It may be safely administered both orally and parenterally. Its activity in the mammalian body is well known and understood. Colchicine is the preferred agent for use in this invention because it is readily available at reasonable cost and is extremely effective for the newly discovered use.

THE INVENTION

It has now been discovered that colchicine may be administered to humans to treat infections caused by a retrovirus of the lentivirus subgroup. It is convenient to administer the colchicine orally, but parenteral administration including intravenous or intramuscular injection may also be employed. The colchicine may also be administered by suppository or in various sustained release compositions including transdermal compositions.

Colchicine may be illustrated by the formula:

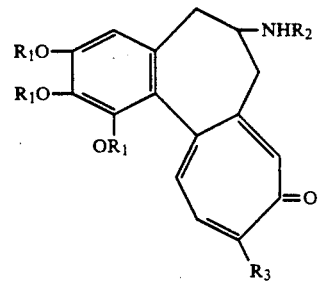

Wherein $R_1$ is $CH_3$, $R_2$ is $COCH_3$; and $R_3$ is $OCH_3$ and thioalkyl containing up to 6 carbon atoms.

As indicated above, there are many steps in the replication of a retrovirus once it has infected the human system. Theoretically, beneficial results could be achieved by any interference which is sufficient to inhibit replication at any one of the stages.

The possible role of the cell's skeletal system, comprising actin like microfilaments, intermediate filaments, and microtubules on viral uptake and morphogenesis has not been extensively studied. Microtubules have been implicated in such phenomena as receptor mobility and protein capping (Edelman, G. M. (1976) Science 192:218-226) and intracellular transport and exocytosis. For a review of this subject, see Malkiason, F. D. (1982) Arch. Dermatol. 118, 456. The effect of microtubular depolymerizing agents including colchicine on the morphogenesis of a limited number of enveloped viruses has been investigated in cell cultures. The results have varied. The drugs were without effect on rhabdovirus, vesicular stomatitis (Gentry, N. and Bussereau, F. (1980) J. Virol, 34: 277) while conversely, the alphavirus Semliki forest virus was inhibited (Richardson, C. D. and Vance, D. E. (1978) J. Biol. Chem. 253:4584–4589). In a cell line chronically infected with Maloney murine leukemia virus, treatment of cultures with low levels of colchicine resulted in a marked reduction of virus production (Satake and Luftig (1982) J. Gen. Virol. 58:339).

It is clear from the foregoing that knowledge of a drug's errect on the skeletal structure of a cell does not provide a basis for predicting the capacity of the drug to interfere usefully with the ability of an infecting virus to replicate and spread an infection.

To establish the efficacy of colchicine for inhibiting replication of retrovirus of the lentivirus subclass, $T_4$ lymphoblastoid cell lines, specifically the known and readily available H9 cell line known to be presistently infected with HIV-1 (Popovic et al (1984) Science 224:498) were employed together with the known uninfected cell lines HUT and CEM.

All cell lines were maintained by removing the supernatant medium every 4 days and replacing it with fresh growth medium, namely RPMI 1640 containing 10% fetal calf serum, 10,000 units/ml penicillin and 50 ugms/ml of streptomycin. RPMI is a standard growth medium which may be obtained from Gibco Labs. It contains a mixture of amino acids, vitamins, glucose, and balanced inorganic salts buffered with sodium phosphate and sodium bicarbonate.

The drug, colchicine obtained from Lilly Co. Indianapolis, Ind. as an intravenous preparation at a concentration of 0.5 mg/ml was appropriately diluted with RPMI and added to the culture medium at levels of 0.1, 1.0 and 10 um which are equivalent to achievable plasma levels in humans. Cells were either pretreated for 60 minutes with colchicine prior to infection with further addition of the drug to the maintenance medium or alternatively, colchicine was added to the maintenance medium and subsequently included in each medium change at 4 day intervals. Cultures were observed usually over a period 20 days and, in some experiments to day 24 past infection. Cell viability was measured by the standard trypan blue exclusion test.

Viral replication was assessed by measurement of the concentration of specific structural components of retrovirus particles that are released into the culture supernatants. These are RT and P24 antigen. The P24 antigen is a viral specific protein associated with the core structure (nucleoid) of the virus particle.

For the measurements, viral RT and P24 are harvested from the culture medium by precipitation or centrifugation. The precipitation of particles from cell free supernates was carried out using polyethylene glycol 6000 and sodium chloride overnight in the cold followed by centrifugation at 2500 rpm at 4° C. for 30 minutes following the procedure of Popovic, supra.

RT was measured by the procedure described by Yoshida et al (1982) PNAS USA 79:2031.

According to this procedure, Poly A- dependent RT activities were measured in virus particles preparations derived from cell-free culture medium using the following reaction mixture:

50 ul of 50 mM tris. HCl, ph 7.8, 5 um dithiothreitol; 100 mM KCL; 10 mM $MgCl_2$ 10 um [$^3$H].DTTP (16 Ci per mM); 0.1% Triton X-100 containing 2 ugs of template Primer, 2 ugs of Poly A, 0.4 ugs of dT 12–18 and the appropriate amount of virus preparation (as the source of RT). The reaction mixture is incubated for 1 Hr. at 37° C. and the [$^3$H] d TMP incorporated into polymer was precipitated with 10% trichloracetic acid at 0° C., collected on glass fiber filter and measured in a liquid scintillation counter.

The Abbott antigen kit is readily available commercially. In operation, it is a standard ELISA procedure in which antibodies immobilized on a surface are incubated with a composition under test and, after appropriate washings, again incubated with another antibody which has been labeled with an enzyme label. The enzyme is then released under conditions making its reaction product detectable.

In one test, colchicine at the above mentioned dilutions was added to a growing culture of HIV-1 infected cell line H9. At first testing following the addition of colchicine on day 4, there was a 67% decrease in RT production compared to the control values, and by day 8 the values in the treated lines were less than 10% of the control where it remained for the duration of the culture period.

With P24 the concentration decreased to 50% of the control by day 12 and continued to drop to day 24. On day 24, the measurement showed a slight increase, but this may be attritutable to the measuring procedure which may not be sufficiently sensitive to detect slight variations in concentrations of the viral particles.

In another test the uninfected cell lines HUT and CEM were first pretreated with colchicine at the concentrations described for 1 hour and then washed 3 times with phosphate buffered saline. They were then resuspended in fresh nutrient medium to which supernatant from H9 infected cells was added as a source of virus for infection. Following a 1 hour incubation, additional medium containing colchicine was added either at 0.01 or 0.1 um. These concentrations were maintained throughout the test period and supernatants were tested at 4 day intervals. Pretreatment of the cell lines with colchicine followed by infection of the lines with HIV-1 resulted in a drop in the production of P24 antigen by day 12 and a continued decline through day 24. The reverse transcriptase levels also decreased in a similar fashion.

An effective dose for treating a human afflicted with any of the described infections will vary with a number of factors well known and understood by the physician. These will include, for example, age and weight of the patient and the status of the disease. An effective dose may vary from about 1 to 2 mg daily. The preferred range is 1.2 to 1.6 mg daily.

The oral and parenteral dosage units will be prepared in accordance with standard procedures and will contain the selected active compound as the only or principal active ingredient in the composition. Any of a wide variety of known inert excipients may be employed to prepare compositions useful in the practice of this invention. These include, for example, dextrose, starch, talc, various types of clay, mineral oil, cottonseed or sesame oil, as well as water or various miscible and immiscible aqueous compositions in which the therapeutic agent is soluble or may be suspended with the aid of known surfactants.

For buccal and sublingual administration the active ingredient can be formulated in tablet form with water soluble binding agents such as lactone or other palatable carbohydrates.

For rectal administration suppositories or inserts containing the active ingredient dispersed in such reagents as cocoa butter, petrolatum, or other natural lubricants or in a synthetic emmollient such as polyethylene glucol 1000 or polyethylene glycol 4000 may be used.

It is convenient to administer the colchicine from sustained release dosage forms. This avoids the necessity of constant clock watching or interruption of normal daily activities. A number of compositions suitable for such preparations are known and can be usefully employed.

For oral administration, the colchicine may be in a time disintegrating tablet or pellet coated with various thickness of known materials such as carnauba wax, cellulose esters and ethers, fats, keratin, gluten or various natural or synthetic esters. Tablets in which the colchicine is contained in a slowly dissolving core such as a core of stearic acid or castor oils are useful. Mixed release granule tablets comprising mixtures of the drug itself and the drug in separate particles coated with materials which dissolve at different rates such as dehydrogenated castor oil or fatty acids can also be employed. Alternatively the colchicine can be bound to an ion exchange resin such as a sulfuric acid type cation exchange resin.

A number of transdermal formulations are possible for use in the practice of this invention. They are discrete dosage forms in construction systems which, when applied to the skin deliver the colchicine through the skin at a controlled rate for systemic circulation. The system typically comprises an outer covering barrier, a drug reservoir which may have a rate of release controlling membrane, a contact adhesive applied to some or parts of the system at the system/skin interface and a protective layer which is removed before applying the system.

The drug reservoir is normally some type of polymer matrix such as a polyvinylpyrrolidone or a silicone polymer from which the drug is slowly released. A microporous membrane such as a polypropylene film may serve as a membrane to control the rate of release.

What is claimed is:

1. A method of treating a human patient infected by a retrovirus of the lentivirous group which comprises administering to said human a therapeutically effective amount of colchicine.

2. A method of treating a human patient infected by a retrovirus of the lentivirous group which comprises administering to said human from about 1 to 2 mgs per day of colchicine.

* * * * *